US00PP15759P2

(12) United States Plant Patent
Vandenberg

(10) Patent No.: US PP15,759 P2
(45) Date of Patent: May 10, 2005

(54) ***CHRYSANTHEMUM* PLANT NAMED 'SKY'**

(50) Latin Name: *Chrysanthemum×morifolium*
Varietal Denomination: Sky

(75) Inventor: Cornelis P. Vandenberg, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/839,165

(22) Filed: May 5, 2004

(51) Int. Cl.[7] ..... A01H 5/00

(52) U.S. Cl. ..... Plt./288

(58) Field of Search ..... Plt./288

*Primary Examiner*—Anne Marie Grunberg
*Assistant Examiner*—June Hwu
(74) *Attorney, Agent, or Firm*—C. A. Whealy

(57) ABSTRACT

A distinct cultivar of *Chrysanthemum* plant named 'Sky', characterized by its upright plant habit; dark green-colored foliage; freely flowering habit; decorative quilled-type inflorescences that are about 8.9 cm in diameter; attractive white-colored ray florets; response time about 59 days; strong peduncles; and good postproduction longevity with inflorescences and foliage maintaining good substance and color for about two weeks in an interior environment.

2 Drawing Sheets

Botanical classification/cultivar designation: *Chrysanthemum×morifolium* cultivar Sky.

BACKGROUND OF THE INVENTION

The present invention relates to a new and distinct cultivar of *Chrysanthemum* plant, botanically known as *Chrysanthemum×morifolium* and hereinafter referred to by the name 'Sky'.

The new *Chrysanthemum* is a product of a planned breeding program conducted by the Inventor in Salinas, Calif., and Alva, Fla. The objective of the breeding program is to create new cut *Chrysanthemum* cultivars having inflorescences with desirable colors and good inflorescence form and substance.

The new *Chrysanthemum* originated from a cross-pollination made by the Inventor in October, 1998, in Salinas, Calif. of a proprietary *Chrysanthemum×morifolium* seedling selection identified as code number 0262, not patented, as the female, or seed, parent with a proprietary *Chrysanthemum×morifolium* seedling selection identified as K906, not patented, as the male, or pollen, parent.

The cultivar Sky was discovered and selected by the Inventor as a flowering plant within the progeny of the stated cross-pollination in a controlled environment in Alva, Fla., in November, 1999. The selection of this plant was based on its desirable inflorescence color and good inflorescence form and substance.

Asexual reproduction of the new *Chrysanthemum* by terminal cuttings in a controlled environment in Alva, Fla. since February, 2000, has shown that the unique features of this new *Chrysanthemum* are stable and reproduced true to type in successive generations.

SUMMARY OF THE INVENTION

Plants of the cultivar Sky have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sky'. These characteristics in combination distinguish 'Sky' as a new and distinct cultivar:

1. Upright cut *Chrysanthemum* that is usually grown as a natural spray.
2. Dark green-colored foliage.
3. Freely flowering habit, about seven inflorescences per flowering stem.
4. Decorative quilled-type inflorescences that are about 8.9 cm in diameter.
5. Attractive white-colored ray florets.
6. Response time about 59 days.
7. Strong peduncles.
8. Good postproduction longevity with inflorescences and foliage maintaining good substance and color for about two weeks in an interior environment.

Compared to plants of the female parent selection, plants of the new *Chrysanthemum* have smaller inflorescences and ray florets do not "pink" under low temperature conditions. In addition, plants of the new *Chrysanthemum* are typically grown as natural sprays whereas plants of the female parent selection are typically grown as disbuds.

Compared to plants of the male parent selection, plants of the new *Chrysanthemum* have smaller inflorescences, fewer disc florets per inflorescence and ray florets do not "pink" under low temperature conditions. In addition, plants of the new *Chrysanthemum* are typically grown as natural sprays whereas plants of the male parent selection are typically grown as disbuds.

Plants of the new *Chrysanthemum* can also be compared to plants of the *Chrysanthemum×morifolium* cultivar Spokane, disclosed in U.S. Plant Pat. No. 10,604. In side-by-side comparisons conducted in Alva, Fla., plants of the new *Chrysanthemum* differed from plants of the cultivar Spokane in the following characteristics:

1. Plants of the new *Chrysanthemum* were more vigorous than plants of the cultivar Spokane.

2. Plants of the new *Chrysanthemum* were more freely flowering than plants of the cultivar Spokane.
3. Plants of the new *Chrysanthemum* flowered about five days earlier than plants of the cultivar Spokane.
4. Ray floret color of plants of the new *Chrysanthemum* was whiter than ray floret color of plants of the cultivar Spokane.

BRIEF DESCRIPTION OF THE PHOTOGRAPHS

The accompanying colored photographs illustrate the overall appearance of the new *Chrysanthemum,* showing the colors as true as it is reasonably possible to obtain in colored reproductions of this type. Colors in the photographs may differ slightly from the color values cited in the detailed botanical description which accurately describe the colors of the new *Chrysanthemum.*

The photograph on the first sheet comprises a side perspective view of a typical flowering stem of 'Sky' grown as a natural spray.

The photograph on the second sheet comprises a close-up view of a typical flowering stem of 'Sky' grown as a natural spray.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Madrid, Cundinamarca, Colombia, South America, under conditions which approximate commercial practice in a single-layer polyethylene-covered greenhouse. Two-week old rooted cuttings were planted on Sep. 1, 2003 and received 18 long day/short nights followed by short day/long nights until flowering. Plants were grown as single-stem natural spray cut *Chrysanthemums.* During the production time, the following environmental conditions were measured: day temperatures, 18 to 24° C.; night temperatures, 4 to 12° C.; and light levels, 3,000 to 5,000 foot-candles. Measurements and numerical values represent averages for six to ten typical flowering stems and were taken about nine to ten weeks after the start of short days.

Botanical classification: *Chrysanthemum×morifolium* cultivar Sky.

Commercial classification: Decorative-type cut *Chrysanthemum.*

Parentage:

*Female or seed parent.*—Proprietary *Chrysanthemum× morifolium* seedling selection identified as code number 0262, not patented.

*Male or pollen parent.*—Proprietary *Chrysanthemum× morifolium* seedling selection identified as code number K906, not patented.

Propagation:

*Type.*—Terminal tip cuttings.

*Time to rooting.*—About 10 to 14 days with soil temperatures of 18 to 21° C.

*Root description.*—Fine, fibrous; white in color.

*Rooting habit.*—Freely branching.

Plant description:

*Appearance.*—Herbaceous decorative-type cut flower that is typically grown as a natural spray.

*Flowering stem description.*—Aspect: Erect. Length: About 101 cm. Stem diameter: About 7 mm. Internode length: About 3.75 cm. Texture: Pubescent; longitudinally ridged. Color: Close to 146A.

*Foliage description.*—Arrangement: Alternate. Length: About 7.5 cm. Width: About 4.5 cm. Apex: Mucronate. Base: Truncate. Margin: Palmately lobed; sinuses parallel to divergent. Texture: Upper and lower surfaces pubescent and leathery; veins prominent on lower surface. Color: Developing and fully expanded foliage, upper surface: More green than 147A. Developing and fully expanded foliage, lower surface: More green than 147B. Venation, upper surface: Close to 147A. Venation, lower surface: 147B to 146A. Petiole: Length: About 2 cm. Diameter: About 3 mm. Color: Upper surface: 147A to 146A. Lower surface: 146A to 146B.

Flowering description:

*Appearance.*—Decorative-type inflorescence form with elongated oblong-shaped ray florets. Inflorescences borne on terminals, arising from leaf axils. Disc and ray florets develop acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 59 days later when grown as a natural spray.

*Postproduction longevity.*—In an interior environment, inflorescences and foliage will maintain good color and substance for about two weeks in an interior environment.

*Quantity of inflorescences.*—Freely flowering habit, about seven inflorescences per stem develop.

*Inflorescence size.*—Diameter: About 8.9 cm. Depth (height): About 3.4 cm. Diameter of disc: About 2 mm. Diameter of receptacle: About 7 mm.

*Inflorescence buds.*—Shape: Oblate. Height: About 5 mm. Diameter: About 7 mm. Color: More green than 146A.

*Ray florets.*—Shape: Quilled. Surface: Concave to straight. Length: About 4.6 cm. Width: About 4 mm. Corolla tube length: About 4.3 cm. Apex: Emarginate. Base: Fused. Texture: Smooth, glabrous; satiny; longitudinally ridged. Aspect: Initially incurved; when mature, upright and straight. Number of ray florets per inflorescence: About 235 arranged in numerous rows. Color, when opening and fully opened, upper and lower surfaces: Close to 155D.

*Disc florets.*—Shape: Tubular, elongated. Length: About 4 mm. Width: About 1 mm. Number of disc florets per inflorescence: About five. Color: Immature: Close to 154A. Mature: Apex: Close to 12A. Mid-section: Close to 150D. Base: Close to 155D.

*Phyllaries.*—Quantity per inflorescence: About 30. Length: About 1 cm. Width: About 4 mm. Shape: Deltoid. Apex: Acute. Base: Truncate. Margin: Entire. Texture, upper surface: Smooth, waxy. Texture, lower surface: Pubescent. Color, upper surface: Close to 146A. Color, lower surface: More green than 146A.

*Peduncles.*—Length: First peduncle: About 12.5 cm. Fourth peduncle: About 18.5 cm. Seventh peduncle: About 20 cm. Diameter: About 3 mm. Angle: About 35 to 40° from vertical. Strength: Strong. Texture: Pubescent. Color: Close to 146A.

*Reproductive organs.*—Androecium: Present on disc florets only. Anther color: 12A. Amount of pollen: None observed. Gynoecium: Present on both ray and disc florets.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of 4° C. and high temperatures high temperatures of 35° C.

It is claimed:

1. A new and distinct cultivar of *Chrysanthemum* plant named 'Sky', as illustrated and described.

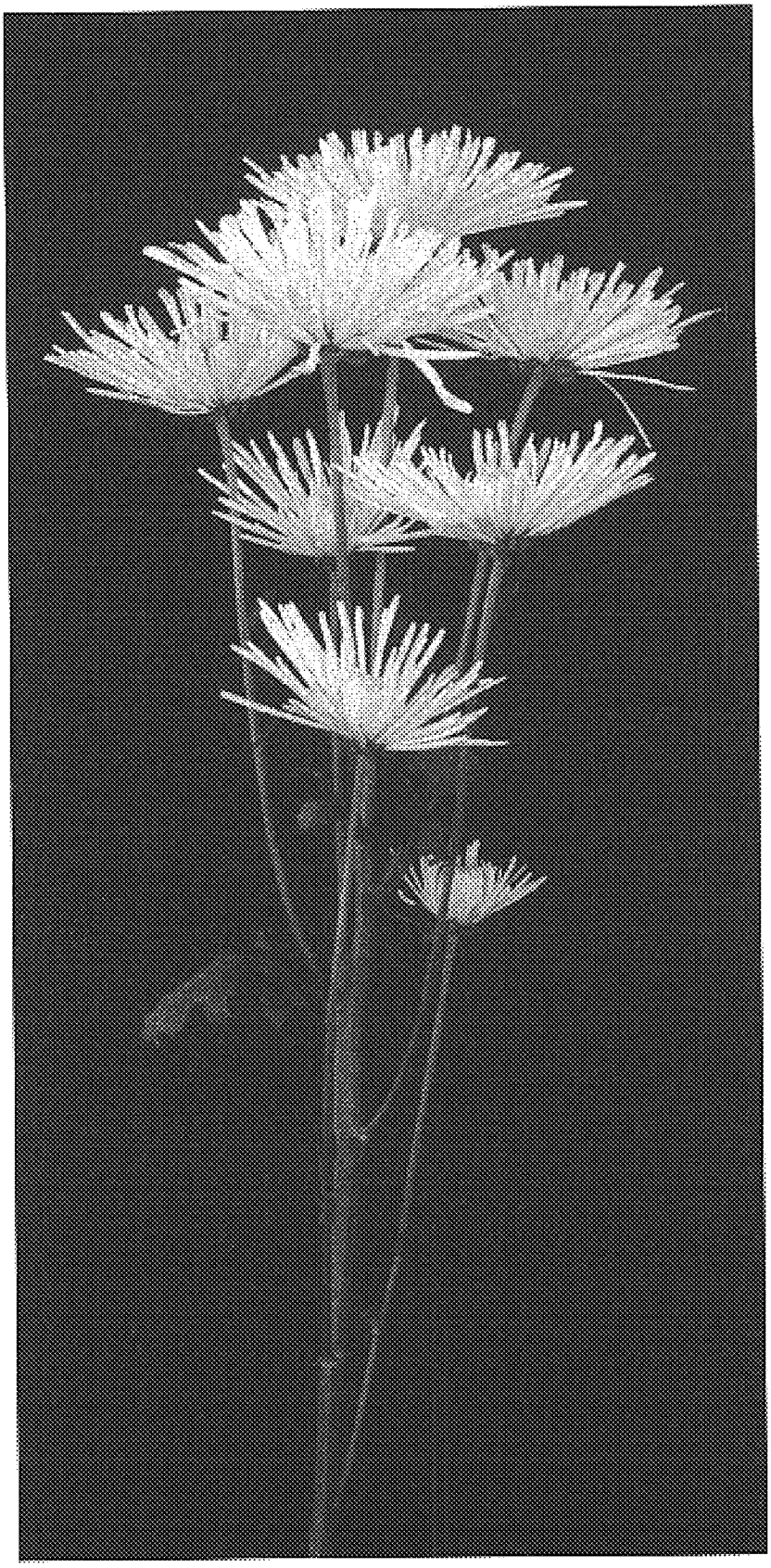

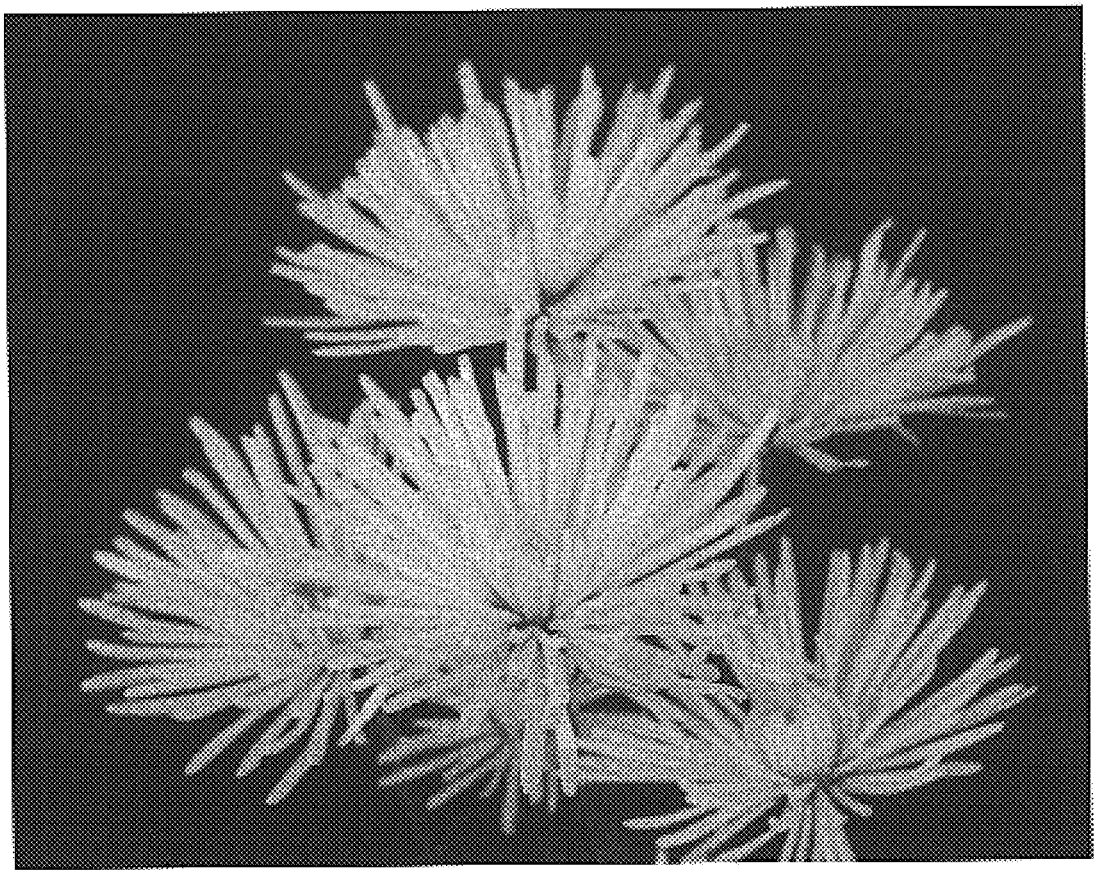

* * * * *